United States Patent [19]

Babasade

[11] Patent Number: 5,574,821
[45] Date of Patent: Nov. 12, 1996

[54] PLUG IN VOLATILE SUBSTANCE DISPENSER AND METHOD FOR DISPENSING VOLATILES

[76] Inventor: Wolfgang Babasade, 405 Knierim Pl., New Milford, N.J. 07646

[21] Appl. No.: 157,882

[22] Filed: Nov. 24, 1993

[51] Int. Cl.⁶ ........................................... A61L 9/03
[52] U.S. Cl. ........................................... 392/392; 392/390
[58] Field of Search ............................ 392/390, 392, 392/395, 403; 439/886

[56] References Cited

U.S. PATENT DOCUMENTS

| | | | |
|---|---|---|---|
| 2,169,055 | 8/1939 | Overshiner | 239/54 |
| 3,748,438 | 7/1973 | Costello | 392/390 |
| 4,391,781 | 7/1983 | van Lit | 392/390 |
| 4,517,308 | 5/1985 | Ehlenz | 502/401 |
| 4,544,592 | 10/1985 | Spector | 239/56 |
| 4,731,520 | 3/1988 | Glucksman | 392/390 |
| 4,837,421 | 6/1989 | Luthy | 392/390 |
| 4,849,606 | 7/1989 | Martens | 392/390 |
| 4,889,286 | 12/1989 | Spector | 239/47 |
| 5,136,684 | 8/1992 | Lonker | 392/392 |

*Primary Examiner*—Teresa J. Walberg

[57] ABSTRACT

A volatile substance dispenser plugs into an electrical outlet to disseminate a vapor into a selected area. After the volatile material is consumed the dispenser is simply discarded. The combined use of a fixed resistor heat pad screen printed within the dispenser, and a thermal conductor, provides unusually uniform heat to a volatile material absorbent substrate within the dispenser, providing economical vaporization of the volatile material. Specific versions of the invention as a fragrance dispenser are described. A unique infant safe electrical connection for the dispenser is also disclosed.

24 Claims, 3 Drawing Sheets

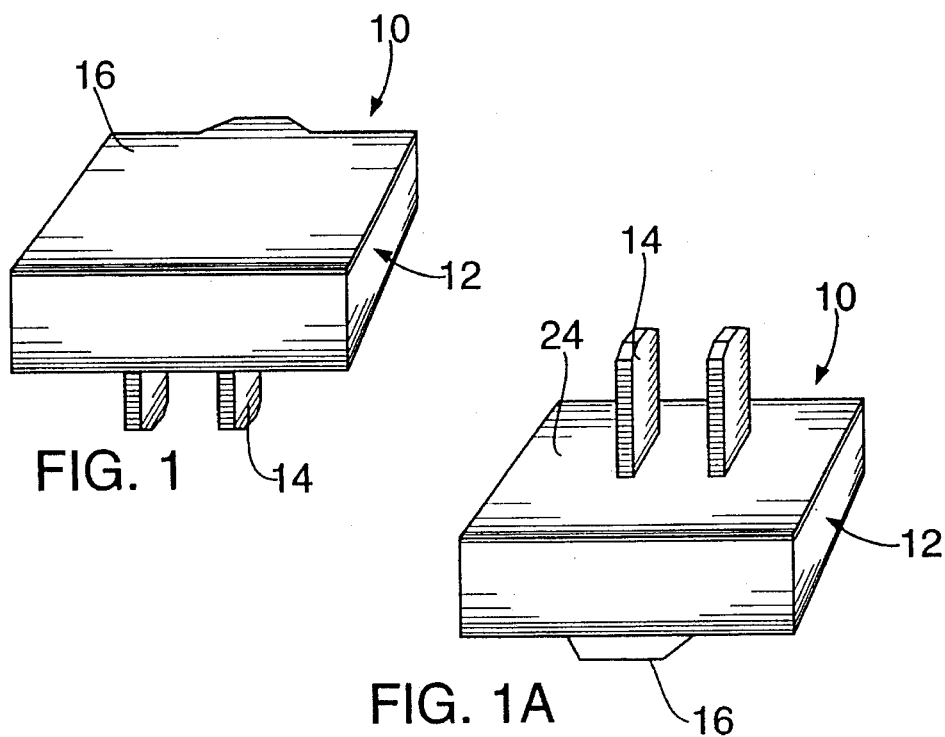
FIG. 1
FIG. 1A
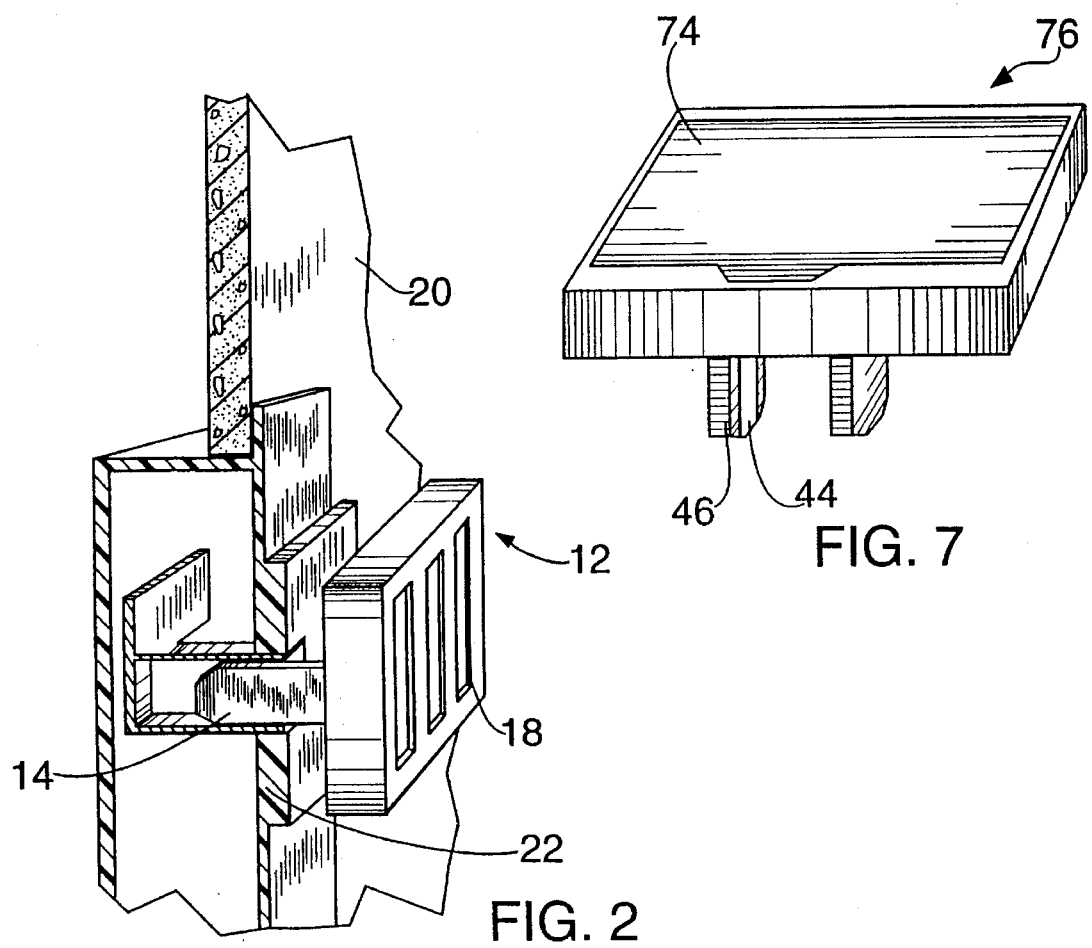
FIG. 7
FIG. 2

PLUG IN VOLATILE SUBSTANCE DISPENSER AND METHOD FOR DISPENSING VOLATILES

BACKGROUND

This invention relates to a volatile substance dispenser and method for dispensing volatile materials, and in particular wherein fragrance is dispensed by means of a fragrance dispenser which is connected to an electrical outlet.

In U.S. Pat. No. 5,230,837, issued Jul. 27, 1993 I disclosed a fragrance dispenser wherein a fragrance wheel was saturated with a selected fragrance material, and then rotated with a motor which could be energized by light falling on a photovoltaic cell. The purpose of this motorized fragrance dispenser was to supply an aromatic substance to a room, such as, for example, a bathroom where masking existing odors is desirable, or the dispenser could be used to dispense insecticides, and so on. While the above referenced invention succeeds in its applications, the instant invention further addresses the requirements of economy for a volatile substance dispenser. For the many applications in which it is desirable or necessary to modify the ambient air characteristics of a room, as, for example, by dispensing volatiles such as fragrances and insecticides, the invention provides a volatile substance dispenser with no moving parts and which simply plugs into a suitable electrical outlet. The dispenser is capable of economies of manufacture which permits discarding the dispenser when the volatile material within the dispenser is consumed.

Devices have been suggested for fragrancing an area as is evident from U.S. Pat. Nos. 4,145,001 and 4,849,606. In U.S. Pat. No. 4,145,001 a method for packaging volatile substances, including fragrance materials, is disclosed. The fragrance material is packaged within two layers of flexible material, the outer layer being impermeable to volatile vapors, and an inner layer being permeable to said vapors. To fragrance an area the outer layer is peeled away, exposing the permeable layer, and this permeable layer then allows the fragrance material to diffuse slowly into the surrounding area over an extended period of time.

In U.S. Pat. No. 4,849,606 a tamper resistant container for fragrancing an area is disclosed. A tray contains the volatile fragrance material, with the top of the tray being secured with a double layer covering. The top layer of the covering is impermeable to the volatile fragrance material. To use this fragrance dispensing device, the top layer is peeled away exposing a second, volatile permeable layer. The tray is then slotted into an outer container equipped with electrical prongs which when connected to an electrical outlet provides heating to Vaporize the volatile fragrance material. When the fragrance material is consumed, the tray is removed from the electrical holder and replaced with a new tray. Before use, the trays remain tamper resistant due to one or more free standing ribs within the tray.

In the instant invention an impermeable protective outer layer of film is removed from the upper surface of the volatile substance dispenser, exposing openings or louvers in this upper surface. The dispenser is then directly connected to a suitable electrical outlet. Gentle heating of a means for retaining the volatile substance is then instantly generated, causing the retained, volatile substance to emit vapors, and thus modify the ambient air within the selected room until the volatile material is consumed. When no longer effective, the volatile substance dispenser is simply discarded. Only extremely low voltage current is generated, making the volatile substance dispenser of the instant invention safe even for accidental handling by infants.

Therefore, it is a primary object of the invention to provide an inexpensive volatile substance dispenser.

A further object is to provide a volatile substance dispenser which is activated when connected to an electrical outlet.

An additional object of the invention is to provide an electrical connection to a volatile substance dispenser that is safe for accidental handling by infants.

Another object of the invention is to provide an inexpensive volatile substance dispenser that can be discarded when no longer effective.

Still another object is to provide for efficient volatilization of a volatile material within a volatile substance dispenser utilizing a minimum quantity of electrical energy.

SUMMARY

These and other objects are obtained in the instant invention of a plug in volatile substance dispenser. This invention provides an integral volatile substance delivery system having a self contained source of heat for activating volatile substance delivery.

For example, in a fragrance dispensing version of the invention, the dispenser is formed in two portions, a bottom portion and a top portion. The bottom portion or base contains two typical metal electrical prongs for connection to an electrical outlet. A portion of the prongs extends into the surface of the base that is to become the interior of the dispenser in order to provide electrical contact with the interior of the dispenser. Two fuse links are affixed to each of the prongs which extend into the interior base surface. A means for depositing a thin film resistive element on this interior surface of this base portion is now employed. This means for depositing a thin film resistive element can be a process known as "Pad Printing" in which a screen printable fixed resistor heat pad emulsion is screen printed over this internal base surface. A thermal coating is applied over this fixed resistor heat pad to encapsulate all of the electrical elements now on the internal base surface, and to insure even heat distribution. The top portion of the dispenser has an upper surface, side walls defining a cavity area, and a substantially open lower surface which provides access to this cavity area. A means for retaining a volatile substance is now placed within this cavity area. This means for retaining a volatile substance can be, for example, an absorbent substrate such as sintered polyethylene having an approximate pore size of 50 to 60 microns. This absorbent substrate is impregnated with up to approximately 4 grams of a selected fragrance oil. The bottom portion and the top portion of the dispenser now snap fit together to form the complete fragrance dispenser. Both the top portion and the bottom portion can be substantially made out of a suitable plastic, such as polyethylene terephthalate, by injection molding. An impermeable film is secured to the outer surface of the upper surface of the top portion to seal the built in openings (or louvers) in this upper surface prior to actually using the dispenser. Now ready to use, this impermeable film is peeled away from the dispenser which can now be plugged into an electrical outlet to fragrance an area until the fragrance material is consumed, where upon the dispenser is discarded. The fragrance absorbing substrate is gently but efficiently heated uniformly with only 0.7 watts/hour, in contrast to the usual at least 1.4 watts/hour required to vaporize the same quantity of fragrance material that is traditional in currently available electrically heated fragrance dispensers.

In a modification of this version of the invention the screen printed, thick film, fixed resistor heat pad and thermal conductor described above is replaced with a chip resistor. This device, with an internal bus bar to insure even heating of the absorbent substrate, is wired to the portion of the prongs which extend into the internal surface of the bottom portion of the fragrance dispenser. This arrangement also yields the same efficiency of current utilization per quantity of fragrance vaporized as described above.

A second version of the invention again has a bottom portion and a top portion. In this case the bottom portion has a solid outer surface, and upstanding side walls defining a cavity area. Again, electrical prongs are affixed to the outer surface of the bottom portion for connection to a suitable electrical outlet. Instead of these prongs being entirely metal, however, they are plastic prongs coated on at least one surface with an electrical conductor. This electrical conductor can be, for example, a polymer silver conductor. Two holes adjacent each prong in the interior surface of the bottom portion provide for running this polymer silver conductor into this interior surface so as to provide electrical contact within the fragrance dispenser. Similarly, an electrical conducting wire arrangement can also be used to make this electrical connection. A fixed resistor heat pad is screen printed onto this interior surface of the bottom portion, and the heat pad is again encapsulated in a thermal conductor. In this version, a fragranced absorbing substrate is now placed within the cavity area within the bottom portion. This absorbing substrate can be made in a variety of ways, such as, for example, an extruded square film of cellulose acetate, a microporous polyolefin plastic film such as "TESLIN" (a registered trademark of and manufactured by PPG Industries), a fragrance impregnated polyethylene film, or utilizing the previously described sintered polyethylene. Finally, a top portion having openings or louvers is snapped onto the bottom portion to form the complete assembly. A vapor impermeable film is secured to the upper surface of the top portion to seal in the volatile fragrance material prior to use. This arrangement again provides for the same economical voltage usage previously described. In addition the elimination of metal prongs for the electrical outlet connection creates unusual safety even when the dispenser is accidentally handled by infants. It should be noted that this uniquely safe electrical plug employed in this volatile substance dispenser can also be used to provide a child safe electrical wall plug in connection with a wide variety of other low level voltage applications such as night lights, electrical alarms, and so on.

In a modification of this version in which the absorbent substrate is placed within a cavity area within the bottom portion of the dispenser, the absorbent substrate in the form of a film or pad is replaced with a tray so that a fragrance gel can be employed. This absorbent substrate can be, for example, fumed silica gel, such as "Cab-O-Sil", available from Cabot Corporation of Toscola, Ill. The gel is mixed with a fragrance oil. In this case a semi-permeable film, such as polyethylene, is heat sealed to the upper surface of the tray, after the fragrance material has been added to the tray, so as to permit the fragrance vapors to diffuse out of the tray at a controlled rate over an extended period of time.

Thus it can be seen that the above described plug in fragrance dispenser provides an economical and convenient method for fragrancing an area. After removal of the impermeable protective film seal, the fragrance dispenser is simply plugged into any suitable electrical outlet, such as a 115 volt, A.C. outlet. When the fragrance is consumed the dispenser is simply discarded. During operation the dispenser provides uniquely efficient and economical fragrance diffusion due to the even heat distribution to the fragrance material within the absorbent substrate. Further, a unique safety feature is provided, even for infants who might accidentally handle the fragrance dispenser while it is plugged into an electrical outlet.

BRIEF DESCRIPTION OF THE DRAWINGS

FIG. 1 is a perspective view of a first version of the fragrance dispenser of the invention.

FIG. 1A is a view of the bottom of the fragrance dispenser of FIG. 1.

FIG. 2 illustrates the fragrance dispenser of FIG. 1 in use connected to an electrical outlet.

FIG. 7 is a perspective view of the fragrance dispenser of FIG. 5.

DETAILED DESCRIPTION

Figure 3:
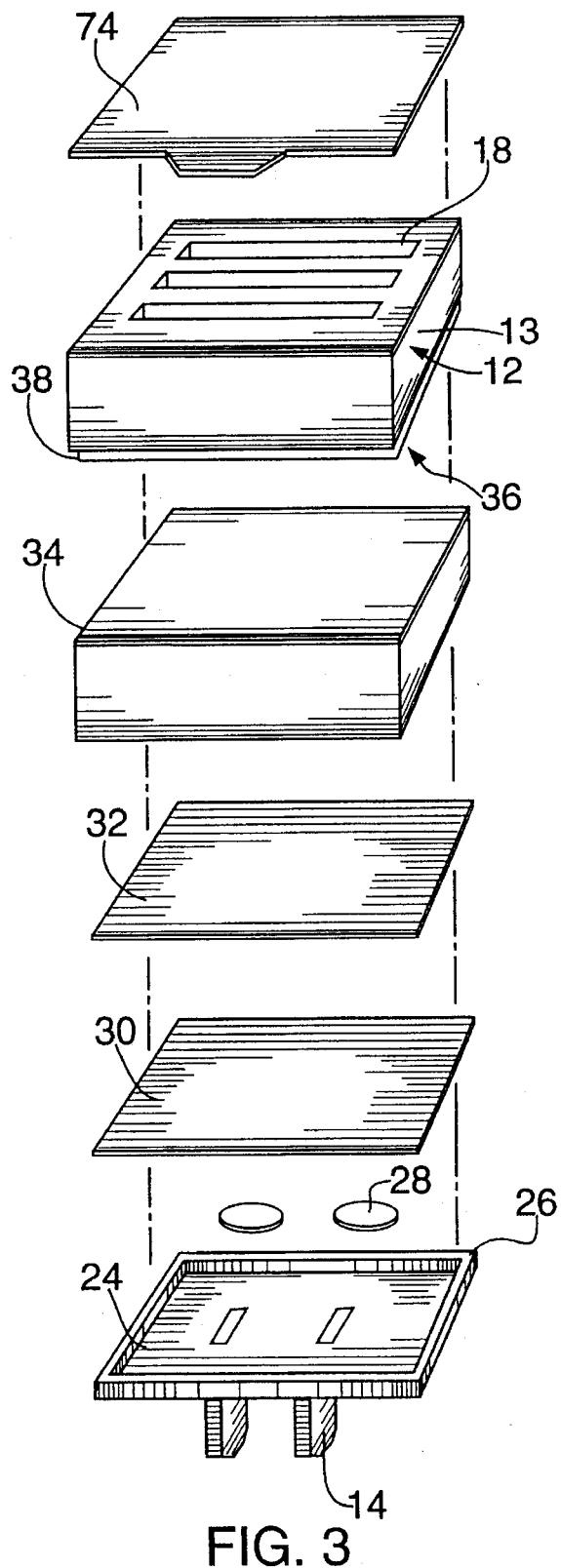
FIG. 3 is an exploded view of the fragrance dispenser of FIGS. 1 and 2.

Referring now to FIGS. 1–4 the volatile substance dispenser is shown in a first version as a fragrance dispenser 10. A top portion 12 has an impermeable, adhesively backed film 16 adhesively secured to the outer surface of the top portion. The purpose of this film 16 is to cover the openings 18 in the upper surface of the top portion so as to prevent fragrance vapors from escaping from the dispenser prior to actual deployment in an area to be fragranced. The bottom portion 24 of the dispenser is shown (FIG. 1A) affixed to the top portion 12. Projecting from the bottom portion 24 are two metal prongs 14. FIG. 2 shows the fragrance dispenser with the prongs 14 connected to a suitable electrical outlet 22, such as a 115 volt, A.C. outlet, located in a wall 20, with the film 16 peeled away to allow for the escape of fragrance vapors. The fragrance dispenser can be shaped in various ways, including the illustrated square shape. Typical dimensions for the complete dispenser 10 are approximately 1½" wide×5/16" deep (top portion 12 and bottom portion 24, exclusive of the prongs 14), with the prongs extending approximately 21/32" from the outer surface of the base portion 24. The top portion 12 and bottom portion 12 of the dispenser are preferably injection molded in a suitable plastic such as polyethylene terephthalate. The impermeable film 16 can be aluminum foil, polypropylene film, or a variety of other suitable materials. The prongs 14 are typical metal prongs suitable for connection to an electrical outlet.

FIG. 3 is an exploded view of the first version of the invention, showing the internal construction of the dispenser. The bottom portion 24 shows the prongs 14 extended into the inner surface of the bottom portion so as to provide electrical contact with the interior of the dispenser. A projection 26 on the periphery of the bottom portion cooperates with a groove 38 on the periphery of the top portion 12 so as to provide a snap fit when the two sections are brought together. A pair of fuse links 30, if desirable for safety reasons, are affixed to the ends of the prongs 14 which project into the internal surface of the bottom portion. A screen printable thick film, fixed resistor heat pad 30 (available from Minico, 50 North Harrison Avenue, P.O. Box 200, Congers, N.Y. 10920) is screen printed over the inner surface of the bottom portion 24. The fixed resistor heat pad has a 10K ohm resistivity. It is screen printed and then fired to 200 degrees centigrade for approximately 10 minutes.

A thermal coating 32 is then applied over the fixed resistor heat pad to serve as an electrically insulating encapsulant for all electrical connections on the inner surface of the bottom portion 12, and to provide for a direction towards even heat distribution of heat to the absorbent substrate during the operation of the dispenser. The thermal conductor is also available from Minico. After application, the thermal conductor is heat cured at 165 degrees centigrade for approximately 25 minutes. Another material that can be employed as a thermal conductor is aluminum nitride. The thermal conductor focuses the generated heat directly upon and uniformly across the absorbent substrate.

Top portion 12 of the fragrance dispenser 10 has an upper surface having openings 18 (FIG. 2) in this upper surface, and upstanding side walls 13 defining a cavity area accessible by opening 36. Particularly suited to this construction is a blotter type of absorbent substrate such as a sintered polyethylene 34 with an average pore size of approximately 50 to 60 microns. Porous polyethylene granules are available from Porex Technologies, 500 Bohannon Road, Fairburn, Ga. 30213-2828. Up to approximately 4 grams of fragrance material is added to this sintered polyethylene 34 absorbent substrate.

The bottom portion 24 and top portion 12 are now snapped together making use of projection 26 in the bottom portion and groove 38 in the top portion, forming the complete fragrance dispenser. When connected to an electrical outlet 0.7 watts/hour is converted to evenly distributed heat to the surface of the sintered polyethylene absorbent substrate for efficient vaporization of a fragrance material.

Figure 4:
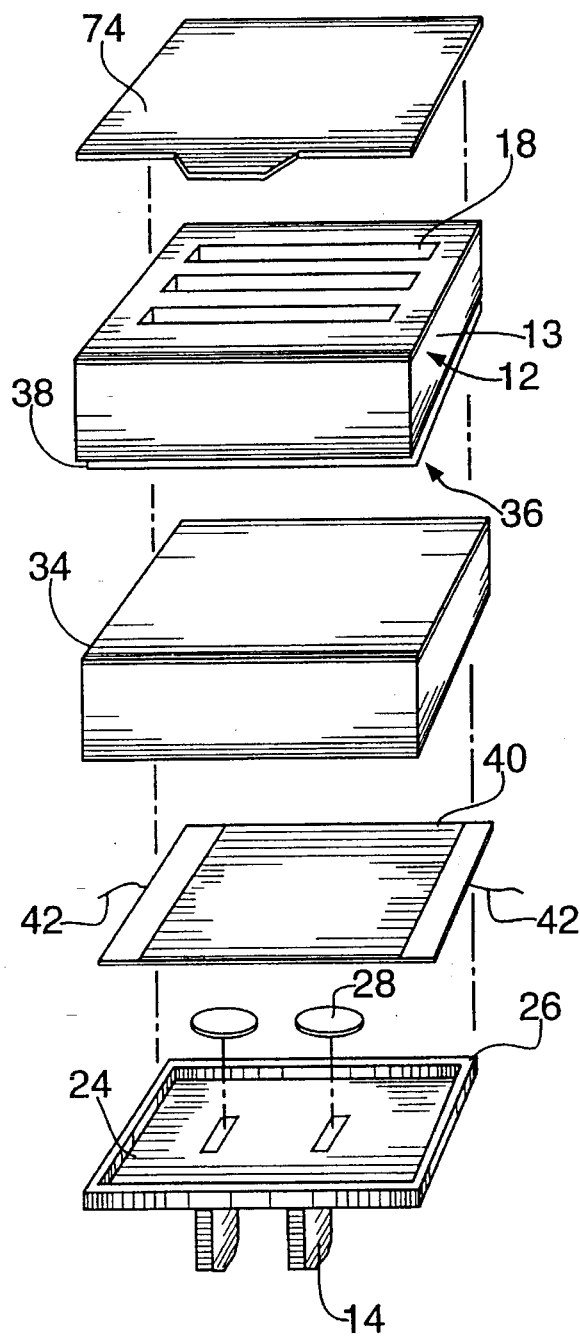
FIG. 4 illustrates a modification of the fragrance dispenser of FIG. 3.

FIG. 4 illustrates a modification of the fragrance dispenser depicted in FIG. 3. In this version the fixed resistor heat pad 30 and the thermal conductor are replaced by a chip resistor 40. This chip resistor has an internal bus bar to insure that incoming electrical current is converted to uniform heat across the surface of the chip resistor that will contact the sintered polyethylene 34 absorbent substrate during operation of the fragrance dispenser. Wires 42 are employed to connect the chip resistor 40 to the prongs 14 extending into the interior surface of the bottom portion 24. After connecting the bottom and top portions together and then connecting the dispenser to a suitable electrical outlet, 0.7 watts/hour is converted to evenly distributed heat to the surface of the sintered polyethylene absorbent substrate.

Figure 5:
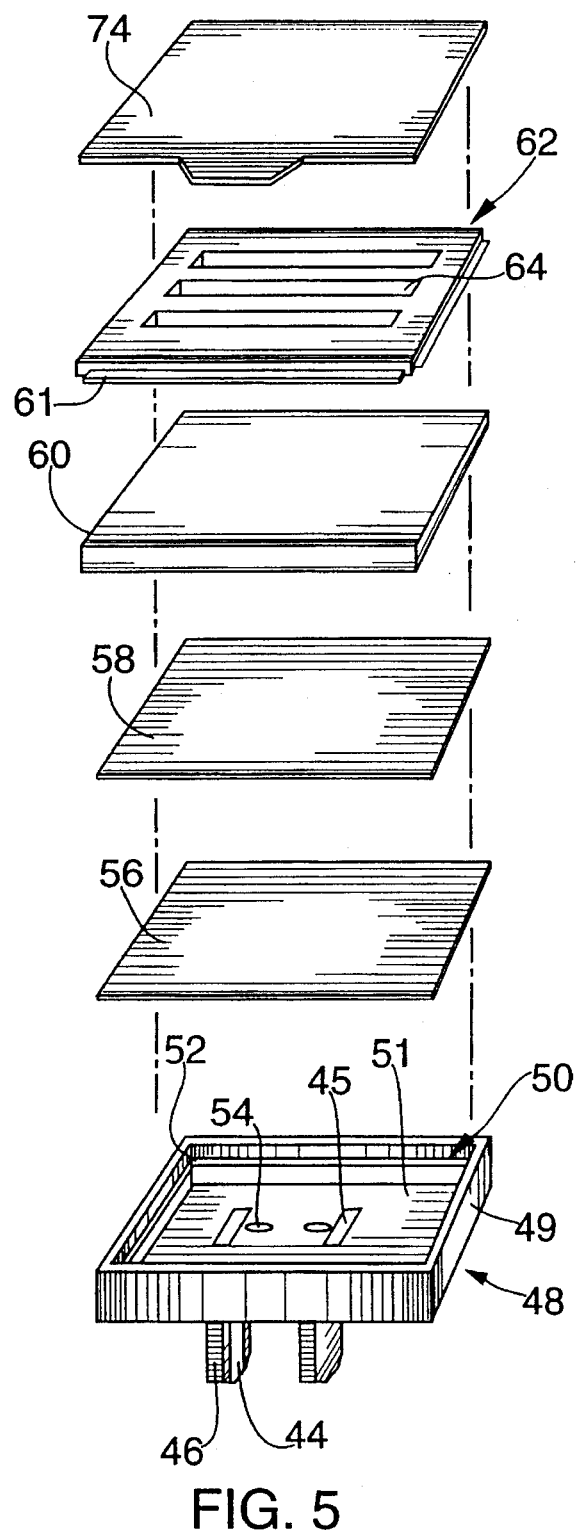
FIG. 5 is an exploded view of a second version of the fragrance dispenser of the invention.
Figure 6:
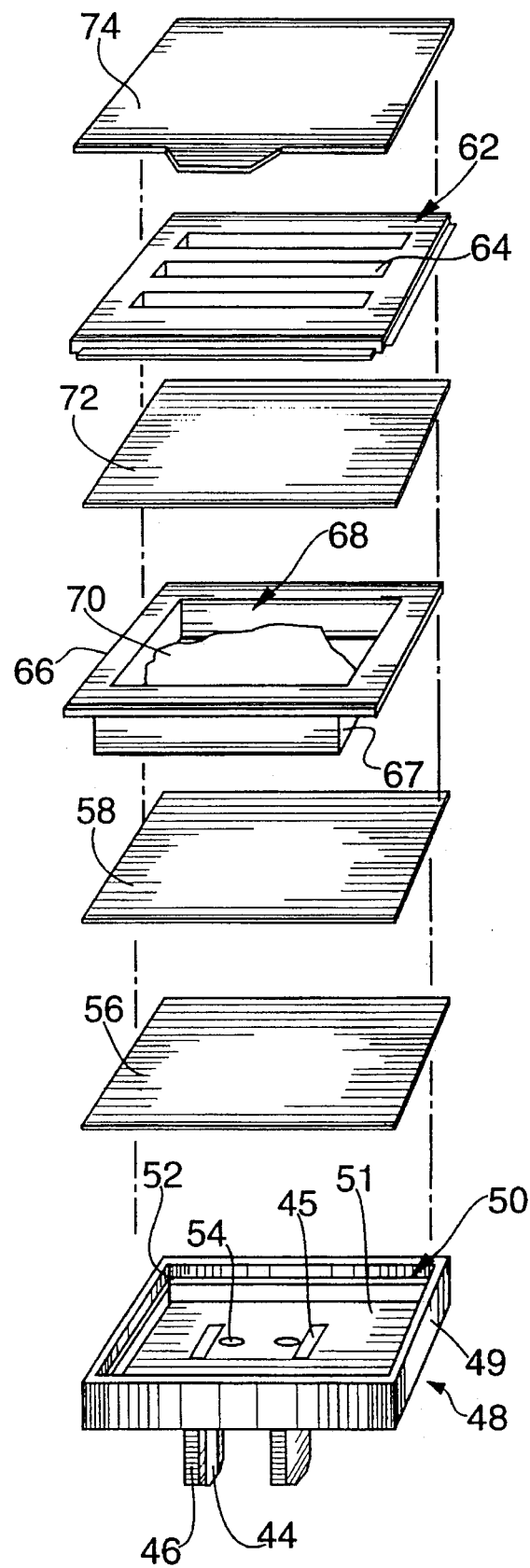
FIG. 6 illustrates a modification of the fragrance dispenser of FIG. 5.

FIGS. 5–7 illustrate a second version 76 (FIG. 7) of the fragrance dispenser of the invention. Again, the dispenser has a bottom portion 48 and a top portion 62. The bottom portion has a base 51, and extending from this base 51 are at least two electrical prongs 46. The prongs 46 are fabricated in plastic with a polymer silver conductor coating 44 on at least one side of each prong, preferably the inwardly facing side. This is M-4000 Polymer Silver Conductor, available from Minico, 50 North Harrison Avenue, P.O. Box 200, Congers, N.Y. 10920. The same polymer silver conductor is affixed to contact tabs 54 within the bottom portion on the internal surface of the base 51 immediately opposite the external points of connection of the prongs. Openings 45 in this internal surface of base 51 permit a polymer silver conductor coating electrical connection between this internal base surface 51 and the externally located prongs. Alternatively a wire or ribbon conductor can be used.

Bottom portion 48 has upstanding side walls defining a cavity area accessed by opening 50. At the periphery of side walls 49 of the bottom portion a groove 52 cooperates with a matching projection 61 on top portion 62 to enable the bottom and top portion to snap fit together. A fixed resistor heat pad 56 is screen printed on the internal surface 51 of the bottom portion 48 as has been previously described for the version of the fragrance dispenser of FIG. 3. A thermal conductor (as previously described for the fragrance dispenser of FIG. 3) is now applied to the fixed resistor heat pad. An absorbent substrate 60 containing approximately 4 grams of a selected fragrance material is now placed within the cavity area of the base portion 48. The absorbent substrate can be made of a variety of materials including cellulose acetate, polyethylene film, microporous polyolefin film such as "TESLIN", TESLIN is a registered trademark of PPG industries, Inc.), and the previously described sintered polyethylene. All of the absorbent substrates and fragrance materials mentioned herein are conventional, and well known to the art. The top portion 62 is now snap fitted into the base portion and when an adhesive backed, impermeable film 74 is secured to the outer surface of the top portion 62 to cover the openings 64 in the top portion 62, a complete fragrance dispenser 76 is formed.

FIG. 6 Illustrates a second version of the fragrance dispenser of FIG. 5. In place of the absorbent substrate 60 film or pad, a tray 66 is provided. The tray has upstanding side walls 67 which define a cavity area accessed by opening 68. In this arrangement a fragrance material may be mixed with a fumed silica 70 placed within the tray. A fumed silica under the name "Cab-O-Sil" is available from Cabot Corporation, Tuscola, Ill. This tray is then covered with a semi-permeable film 72 such as, for example, polyethylene. The semi-permeable film is then heat sealed to the tray. The purpose of this film 72 being to provide controlled diffusion of the fragrance material over a prolonged period of time.

The volatile substance dispenser of the invention provides a new convenience in an integral volatile substance delivery system for economical and efficient dissemination of vapors into an area. Simply removing an adhesive film and plugging the unit into an electrical outlet immediately activates the dispenser. When the volatile substance is consumed in normal use, the dispenser is discarded. Economy in use is provided by the efficient focusing of heat upon the means for holding the volatile substance. For example, in the fragrance dispensers described above only 0.7 watts/hour vaporizes the same quantity of fragrance material which ordinarily requires 1.4 watts/hour in currently available electrically heated fragrance dispensers. In addition the unique plastic prong electrical connection is disclosed, providing an additional safety factor even if the activated dispenser is accidentally handled by infants.

While the present invention has been disclosed in connection with preferred versions shown and described in detail, various modifications and improvements will become readily apparent to those skilled in the art. Accordingly, the spirit and scope of the present invention is to be limited only by the following claims.

What is claimed is:

1. A volatile substance dispenser for direct connection to an electrical outlet, said fragrance dispenser being disposable after a fragrance material has diffused out of said fragrance dispenser after a period of normal use, said fragrance dispenser comprising:

(a) a base portion and a top portion;

(b) said base portion having at least two prongs connected to said base portion for electrically connecting said base portion to said electrical outlet;

(c) said top portion having openings therein to permit vapors to pass through said openings;

(d) a cavity area between said base portion and said top portion when said base portion and said top portion are joined together;

(e) a pre-selected quantity of said volatile substance;

(f) retaining means for retaining said volatile substance, said retaining means having a base and a top;

(g) securing means for securing said retaining means within said cavity area between said top portion and said base portion of said dispenser;

(h) means for carrying electric current from said prongs into said cavity area when said prongs are connected to said electrical outlet; and (i) electrical conversion means for converting said electrical current supplied by said prongs into heat, said electrical conversion means comprising a combination resistive element and a thermal conductor, said thermal conductor having substantially the same surface area as said base of said volatile substance retaining means, so that when said prongs on said base portion are connected to said electrical outlet said electrical conversion means causes said heat to be focused upon, and uniformly distributed across the surface of said base of said means for retaining said volatile material, whereby said volatile substance is caused to be diffused away from said means for retaining said volatile substance in the form of vapors, which vapors now pass through said openings in said top portion of said dispenser, thereby disseminating said vapors in a place wherein said volatile substance dispenser is located.

2. The volatile substance dispenser according to claim 1, further comprising an adhesive backed, vapor impermeable film, said adhesive backed film being adhesively secured to the outwardly facing surface of said top portion of said dispenser so that said openings in said top portion are closed by said impermeable film, said film being capable of being easily peeled off of said outwardly facing surface of said top portion when said volatile substance dispenser is to be employed to disseminate said vapors in a selected place.

3. The volatile substance dispenser according to claim 1 wherein said electrical outlet is a typical 115 volt, A.C. outlet.

4. The volatile substance dispenser according to claim 1 wherein said volatile substance is a fragrance material.

5. The fragrance dispenser according to claim 4 wherein said means for retaining said volatile material is an absorbent substrate.

6. The fragrance dispenser according to claim 5 wherein said absorbent substrate is sintered polyethylene having an average pore size between 50 and 60 microns.

7. The fragrance dispenser according to claim 5 wherein said absorbent substrate is a porous, plastic film.

8. The fragrance dispenser according to claim 7 wherein said plastic film is microporous, polyolefin.

9. The fragrance dispenser according to claim 7 wherein said plastic film is cellulose acetate.

10. The fragrance dispenser according to claim 7 wherein said absorbent substrate is a fragrance impregnated polyethylene plastic film.

11. The fragrance dispenser according to claim 1 wherein said means for securing said retaining means includes a tray for holding said retaining means, said retaining means being an absorbent substrate, said tray having a base and a top.

12. The fragrance dispenser according to claim 11 further comprising a semi-permeable film affixed to said tray, said semi-permeable film providing for controlled diffusion of fragrance vapors from said tray over a pre-determined period of time.

13. The fragrance dispenser according to claim 11 wherein said absorbent substrate is a silica gel in which a fragrance oil has been mixed.

14. A volatile substance dispenser for direct connection to an electrical outlet, said fragrance dispenser being disposable after a fragrance material has diffused out of said fragrance dispenser after a period of normal use, said fragrance dispenser comprising:

(a) a base portion and a top portion;

(b) said base portion having at least two prongs connected to said base portion for electrically connecting said base portion to said electrical outlet;

(c) said top portion having openings therein to permit vapors to pass through said openings;

(d) a cavity area between said base portion and said top portion when said base portion and said top portion are joined together;

(e) a pre-selected quantity of said volatile substance;

(f) retaining means for retaining said volatile substance, said retaining means having a base and a top;

(g) securing means for Securing said retaining means within said cavity area between said top portion and said base portion of said dispenser;

(h) means for carrying electric current from said prongs into said cavity area when said prongs are connected to said electrical outlet; and (i) electrical conversion means for converting said electric current supplied by said prongs into heat, said electrical conversion means comprising a thick film, fixed resistor heat pad and a thermal conductor, said fixed resistor heat pad being affixed to an interior surface of said base portion which is immediately adjacent said cavity area within said volatile substance dispenser, said fixed resistor heat pad being screen printed on said interior surface of said base portion, said fixed resistor heat pad being in electrical contact with said prongs connected to said base portion, said thermal conductor being within said cavity area positioned between said fixed resistor heat pad and said means for retaining said volatile substance, said thermal conductor having substantially the same surface area as said base of said volatile substance retaining means, so that when said current is converted to said heat, said heat is focused upon and uniformly distributed across the surface of said base of said volatile substance retaining means, whereby said volatile substance is caused to be diffused away from said means for retaining said volatile substance in the form of vapors, which vapors now pass through said openings in said top portion of said dispenser, thereby disseminating said vapors in a place wherein said volatile substance dispenser is located.

15. The volatile substance dispenser according to claim 14 wherein said electrical conversion means is a chip resistor, said chip resistor having means for being electrically wired to said prongs, said chip resistor having means for converting said electric current into heat and supplying said heat uniformly across the surface of said base of said means for retaining said volatile substance.

16. The volatile substance dispenser according to claim 15 wherein said chip resistor converts 0.7 watts/hour of said electric current into said heat.

17. The volatile substance dispenser according to claim 14 wherein said thermal conductor is fabricated of aluminum nitride.

18. The volatile substance dispenser according to claim 14 wherein said thick film, fixed resistor heat pad converts 0.7 watts/hour of said electric current into said heat.

19. The volatile substance dispenser according to claim 14 wherein said prongs are fabricated of a suitable plastic, said prongs having a first electrically conductive coating on at least one side of said prongs, said prongs and said coating being in direct connection with a second electrically conductive coating affixed to said interior surface of said base portion.

20. The volatile substance dispenser according to claim 19 wherein said first electrically conductive coating on at least one side of said prongs is on the inwardly facing side of said prongs so that said first electrically conductive coatings are facing each other.

21. The volatile substance dispenser according to claim 19 wherein said first and second electrically conductive coatings are an electrical conductor substantially filled with silver.

22. A method for disseminating a volatile substance within a selected area, comprising the steps of:

connecting a volatile substance dispenser to an electrical outlet, said dispenser having a body the interior of which contains a porous pad saturated with a pre-selected volatile material, said body having at least two built-in prongs for making said connection to said outlet;

causing an electric current to flow into the interior of said dispenser through said prongs and within a portion of said interior of said dispenser warming said porous pad as said current flows through a thick film, fixed resistor heat pad within said interior of said dispenser, thereby creating heat within said interior of said dispenser, said heat being focused upon and directed across the surface of said porous pad, thereby vaporizing said pre-selected volatile material, and allowing said vapors to escape from said dispenser and to be disseminated within said selected area.

23. The method according to claim 22 wherein said volatile substance is a fragrance material, which upon being vaporized causes said selected area to be fragranced.

24. The method according to claim 22 further comprising the step of uniformly warming said porous pad utilizing a thermal conducting film placed between said fixed resistor heat pad and said porous pad within said dispenser.

* * * * *